(12) United States Patent
Rostovtsev et al.

(10) Patent No.: US 8,158,831 B2
(45) Date of Patent: Apr. 17, 2012

(54) CHRYSENE COMPOUNDS FOR DEEP BLUE LUMINESCENT APPLICATIONS

(75) Inventors: Vsevolod Rostovtsev, Swarthmore, PA (US); Reid John Chesterfield, Wilmington, DE (US); Norman Herron, Newark, DE (US); Kerwin D. Dobbs, Wilmington, DE (US); Jeffrey A. Merlo, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/129,760

(22) Filed: May 30, 2008

(65) Prior Publication Data

US 2008/0306303 A1    Dec. 11, 2008

Related U.S. Application Data

(60) Provisional application No. 60/941,383, filed on Jun. 1, 2007.

(51) Int. Cl.
    *C07C 211/00*    (2006.01)
(52) U.S. Cl. ......................................... 564/426; 564/305
(58) Field of Classification Search .................. None
    See application file for complete search history.

(56) References Cited

U.S. PATENT DOCUMENTS

| | | | |
|---|---|---|---|
| 4,043,311 A | 8/1977 | Bieri | |
| 5,247,190 A | 9/1993 | Friend et al. | |
| 5,408,109 A | 4/1995 | Heeger et al. | |
| 6,670,645 B2 | 12/2003 | Grushin et al. | |
| 6,852,429 B1 | 2/2005 | Li et al. | |
| 6,875,524 B2 | 4/2005 | Hatwar et al. | |
| 7,075,102 B2 | 7/2006 | Grushin et al. | |
| 7,173,131 B2 | 2/2007 | Saitoh et al. | |
| 7,358,409 B2 | 4/2008 | Saitoh et al. | |
| 7,375,250 B2 | 5/2008 | Saitoh et al. | |
| 7,491,450 B2 | 2/2009 | Okinaka et al. | |
| 7,651,788 B2 | 1/2010 | Seo et al. | |
| 7,709,104 B2 | 5/2010 | Saitoh et al. | |
| 2002/0076576 A1 | 6/2002 | Li | |
| 2003/0072966 A1 | 4/2003 | Hosokawa et al. | |
| 2004/0102577 A1 | 5/2004 | Hsu et al. | |
| 2004/0106003 A1 | 6/2004 | Chen et al. | |
| 2004/0121184 A1 | 6/2004 | Thompson et al. | |
| 2004/0127637 A1 | 7/2004 | Hsu et al. | |
| 2005/0031898 A1 | 2/2005 | Li et al. | |
| 2005/0064233 A1 | 3/2005 | Matsuura et al. | ............ 428/690 |
| 2005/0158577 A1 | 7/2005 | Ishibashi et al. | |
| 2005/0184287 A1 | 8/2005 | Herron et al. | |

(Continued)

FOREIGN PATENT DOCUMENTS

EP    443 861 B1    8/1991
(Continued)

OTHER PUBLICATIONS

Written Opinion of the International Searching Authority, PCT/US2008/065091, PCT counterpart of the present application, Dec. 1, 2009.

(Continued)

*Primary Examiner* — Daniel Sullivan
*Assistant Examiner* — Clinton Brooks

(57) ABSTRACT

This disclosure relates to chrysene compounds with deep blue emission that are useful in electroluminescent applications. It also relates to electronic devices in which the active layer includes such a chrysene compound.

12 Claims, 1 Drawing Sheet

U.S. PATENT DOCUMENTS

| | | | |
|---|---|---|---|
| 2005/0205860 | A1 | 9/2005 | Hsu et al. |
| 2006/0033421 | A1 | 2/2006 | Matsuura et al. |
| 2006/0052641 | A1 | 3/2006 | Funahashi |
| 2006/0113528 | A1 | 6/2006 | Okinaka et al. |
| 2006/0115678 | A1 | 6/2006 | Saitoh et al. |
| 2006/0121312 | A1 | 6/2006 | Yamada et al. |
| 2006/0152146 | A1* | 7/2006 | Funahashi ............ 313/504 |
| 2006/0159838 | A1 | 7/2006 | Kowalski et al. |
| 2006/0194074 | A1 | 8/2006 | Funahashi |
| 2006/0210830 | A1 | 9/2006 | Funahashi et al. ........ 428/690 |
| 2006/0267488 | A1 | 11/2006 | Saitoh et al. |
| 2007/0063638 | A1 | 3/2007 | Tokairin et al. |
| 2007/0114917 | A1 | 5/2007 | Funahashi |
| 2007/0236137 | A1 | 10/2007 | Funahashi |
| 2007/0255076 | A1 | 11/2007 | Ito et al. |
| 2007/0292713 | A9 | 12/2007 | Dobbs et al. |
| 2007/0298530 | A1 | 12/2007 | Feehery |
| 2008/0049413 | A1 | 2/2008 | Jinde et al. |
| 2008/0071049 | A1 | 3/2008 | Radu et al. |
| 2008/0191614 | A1 | 8/2008 | Kim et al. |
| 2008/0233433 | A1 | 9/2008 | Igarashi et al. |
| 2008/0286605 | A1 | 11/2008 | Takeda |
| 2008/0303425 | A1 | 12/2008 | Rostovtsev et al. |
| 2009/0058279 | A1 | 3/2009 | Takeda |

FOREIGN PATENT DOCUMENTS

| | | | |
|---|---|---|---|
| EP | 1 061 112 A | | 12/2000 |
| EP | 1 561 794 A | | 8/2005 |
| EP | 1561 794 A | | 8/2005 |
| EP | 2067766 A1 | | 6/2009 |
| EP | 2067767 A1 | | 6/2009 |
| JP | 07249490 A | | 9/1995 |
| JP | EP1561794 | * | 10/2003 |
| JP | 200410550 A | | 1/2004 |
| JP | 2006052323 A | | 2/2006 |
| JP | 2006151844 A | | 6/2006 |
| JP | 2006219392 A | | 8/2006 |
| JP | 2007186449 A | | 7/2007 |
| JP | 2009161470 A | | 7/2009 |
| KR | 20090046731 A | | 5/2009 |
| KR | 20090086015 A | | 8/2009 |
| KR | 20090086920 A | | 8/2009 |
| KR | 20090093897 A | | 9/2009 |
| WO | 03040257 A1 | | 5/2003 |
| WO | 03063555 A1 | | 7/2003 |
| WO | 2004016710 A1 | | 2/2004 |
| WO | 2005052027 A1 | | 6/2005 |
| WO | WO2006025273 | * | 3/2006 |
| WO | 2007021117 A1 | | 2/2007 |
| WO | 2007100096 A1 | | 9/2007 |
| WO | 2007105917 A1 | | 9/2007 |
| WO | 2007108666 A1 | | 9/2007 |
| WO | 2008149968 A1 | | 12/2008 |
| WO | 2009018009 A1 | | 2/2009 |
| WO | 2009028902 A2 | | 3/2009 |
| WO | 2009055628 A1 | | 4/2009 |
| WO | 2009028902 A3 | | 6/2009 |

OTHER PUBLICATIONS

CRC Handbook of Chemistry and Physics, 81st Edition, 2000, (Book Not Included).

John Markus, Photoconductive Cell, Electronics and Nucleonics Dictionary, 1966, pp. 470, 471 & 476, McGraw-Hill.

Gustafsson et al., Flexible Light-Emitting Diodes Made From Soluble Conducting Polymers, Nature, 1992, vol. 357:477-479.

Y. Wang, Photoconductive Polymers, Kirk-Othmer Encyclopedia of Chemical Technology, 4th Edition, 1996, vol. 18:837-860.

Negishi et al; III.2.15 Palladium-Catalyzed Conjugate Substitution; Handbook of Organopalladium Chemistry for Organic Synthesis, 2000 vol. 1 pp. 767-789.

Beckmann et al; Methyl reorientation in solid 3-ethylchrysene and 3-isopropylchrysene; 1998; vol. 12; pp. 251-256.

Kodomari et al; Selective Halogenation of Aromatic Hydrocarbons with Alumina-Supported Corrper (II) Halides, J. Org. Chem. 1988 vol. 53 pp. 2093-2094.

International Search Report, European Patent Office, Rijswijk NL, in PCT/2008/063811, PCT copending U.S. Appl. No. 12/121,883, Csaba A. Nemes, Authorized Officer, Jul. 29, 2008.

International Search Report, European Patent Office, Rijswijk NL, in PCT/2008/065187, PCT copending U.S. Appl. No. 12/129,753, Cecile Vanier, Authorized Officer Feb. 10, 2008.

International Search Report, Korean Intellectual Property Office, Daejeon, Republic of Korea, in PCT/2009/065163, PCT copending U.S. Appl. No. 13/120,001, Hyun Shik Oh, Authorized Officer, May 19, 2010.

International Search Report, Korean Intellectual Property Office, Daejeon, Republic of Korea, in PCT/2010/040578, PCT copending application, Hyun Shik Oh, Authorized Officer, Feb. 11, 2011.

International Search Report, Korean Intellectual Property Office, Daejeon, Republic of Korea, in PCT/2009/068956, PCT copending U.S. Appl. No. 12/643,487, Hyun Shik Oh, Authorized Officer, Sep. 6, 2010.

International Search Report, Korean Intellectual Property Office, Daejeon, Republic of Korea, in PCT/2009/068918, PCT copending U.S. Appl. No. 12/643,403, Jun Gyu Kim, Authorized Officer, Jul. 26, 2010.

International Search Report, Korean Intellectual Property Office, Daejeon, Republic of Korea, in PCT/2010/025764, PCT copending U.S. Appl. No. 12/714,880, Hyun Shik Oh, Authorized Officer, Sep. 27, 2010.

International Search Report, Korean Intellectual Property Office, Daejeon, Republie of Korea, PCT/US2009/068921, PCT copending U.S. Appl. No. 12/643,486, Hyun Shik Oh, Authorized Officer, Aug. 5, 2010.

International Search Report, Korean Intellectual Property Office, Daejeon, Republic of Korea, in PCT/2009/068922, PCT copending U.S. Appl. No. 12/643,567, Hyun Shik Oh, Authorized Officer, Oct. 20, 2010.

International Search Report, Korean Intellectual Property Office, Daejeon, Republic of Korea, in PCT/2009/068928, PCT copending U.S. Appl. No. 12/643,511, Hyun Shik Oh, Authorized Officer, Aug. 17, 2010.

International Search Report, Korean Intellectual Property Office, Daejeon, Republic of Korea, in PCT/2010/035356, PCT copending U.S. Appl. No. 12/782,781, Hyun Shik Oh, Authorized Officer, Dec. 12, 2010.

International Search Report, Korean Intellectual Property Office, Daejeon, Republic of Korea, in PCT/2009/068945, PCT copending U.S. Appl. No. 12/643,420, Hyun Shik Oh, Authorized Officer, Sep. 27, 2010.

International Search Report, Korean Intellectual Property Office, Daejeon, Republic of Korea, in PCT/2009/068950, PCT copending U.S. Appl. No. 12/643,449, Hyun Shik Oh, Authorized Officer, Jan. 3, 2011.

International Search Report, Korean Intellectual Property Office, Daejeon, Republic of Korea, in PCT/2009/068976, PCT copending U.S. Appl. No. 12/643,515, Bum Soo Kim, Authorized Officer, Jan. 28, 2011.

International Search Report, Korean Intellectual Property Office, Daejeon, Republic of Korea, Hyun Shik Oh, Authorized Officer, Aug. 13, 2010 in PCT/US2009/069255, PCT counterpart of the present application.

International Search Report, European Patent Office, Rijswijk NL, in PCT/2008/065091, PCT corresponding U.S. Appl. No. 12/129,760, Alina Sen, Authorized Officer, Oct. 23, 2008.

Mueller et al, Synthesis and Characterization of Soluble Oligo(9,10-anthrylene)s, Chem. Ber. 1994, 127, pp. 437-444.

International Search Report Korean Intellectual Property Office, Daejeon, Republic of Korea, Hyun Shik Oh, Authorized Officer, Dec. 24, 2010, in PCT/US10/035364.

* cited by examiner

CHRYSENE COMPOUNDS FOR DEEP BLUE LUMINESCENT APPLICATIONS

RELATED APPLICATION DATA

This application claims priority under 35 U.S.C. §119(e) from U.S. Provisional Application No. 60/941,383 filed on Jun. 1, 2007, which is incorporated by reference herein in its entirety.

BACKGROUND

1. Field of the Disclosure

This disclosure relates to electroluminescent chrysene compounds that have deep blue emission. It also relates to electronic devices in which the active layer includes such a chrysene compound.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. No. 5,247,190, U.S. Pat. No. 5,408,109, and Published European Patent Application 443 861.

However, there is a continuing need for electroluminescent compounds, especially compounds that are blue-emitting.

SUMMARY

There is provided a compound having Formula I:

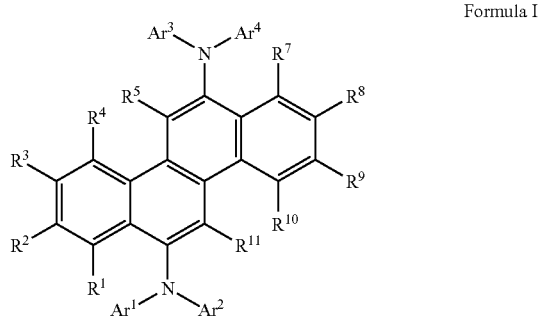

Formula I wherein:
  Ar1 and Ar3 are the same or different and are aryl, and at least one of Ar1 and Ar3 has at least one electron-withdrawing substituent;
  Ar2 and Ar4 are the same or different and are aryl;
  R1, R2, and R4 are the same or different and are selected from the group consisting of H and an electron-withdrawing group;
  R3 is an electron-withdrawing group;
  R5 and R7 through R11 are the same or different and are selected from the group consisting of H and alkyl;
  wherein said compound is capable of emitting deep blue light.

There is also provided an electronic device comprising an active layer comprising the compound of Formula I.

BRIEF DESCRIPTION OF THE DRAWINGS

Embodiments are illustrated in the accompanying figures to improve understanding of concepts as presented herein.

Figure 1:
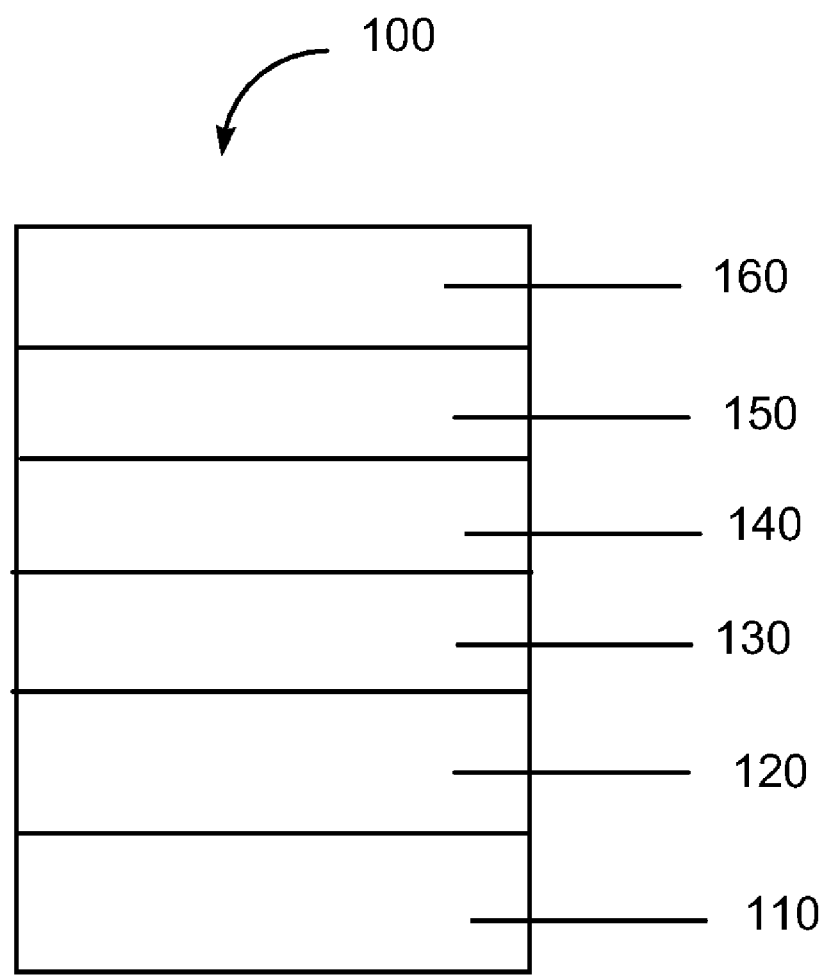
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DEFINITION OF TERMS

As used herein, the term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity.

The term "electron-withdrawing" as it refers to a substituent group is intended to mean a group which decreases the electron density of an aromatic ring.

The term "aryl" is intended to mean a group derived from an aromatic hydrocarbon having one point of attachment. The term includes groups which have a single ring and those which have multiple rings which can be joined by a single bond or fused together. The term is intended to include heteroaryls. The term "arylene" is intended to mean a group derived from an aromatic hydrocarbon having two points of attachment. In some embodiments, an aryl group has from 3-60 carbon atoms.

The term "alkyl" is intended to mean a group derived from an aliphatic hydrocarbon having one point of attachment, and includes a linear, a branched, or a cyclic group. The term is intended to include heteroalkyls. The term "alkylene" is intended to mean a group derived from an aliphatic hydrocarbon and having two or more points of attachment. In some embodiments, an alkyl group has from 1-20 carbon atoms.

The term "binaphthyl" is intended to mean a group having two naphthalene units joined by a single bond. In some embodiments, the binaphthyl group is 1,1-binaphthyl, which is attached at the 3-, 4-, or 5-position; in some embodiments, 1,2-binaphthyl, which is attached at the 3-, 4-, or 5-position on the 1-naphthyl moiety, or the 4- or 5-position on the 2-naphthyl moiety; and in some embodiments, 2,2-binaphthyl, which is attached at the 4- or 5-position.

The term "biphenyl" is intended to mean a group having two phenyl units joined by a single bond. The group can be attached at the 2-, 3-, or 4-position.

The term "deep blue" refers to radiation that has an emission maximum of photoluminescence at a wavelength in a range of approximately 400-475 nm. In some embodiments, deep blue light has color coordinates of x=0.1-0.2, and y<0.1, according to the C.I.E. chromaticity scale (Commision Internationale de L'Eclairage, 1931).

The prefix "fluoro" indicates that one or more available hydrogen atoms in a compound have been replaced with F. The prefix "perfluoro" indicates that all available hydrogen atoms have been replace with F.

The prefix "hetero" indicates that one or more carbon atoms have been replaced with a different atom. In some embodiments, the different atom is N, O, or S.

All groups may be unsubstituted or substituted. In some embodiments, the substituents are selected from the group consisting of halide, alkyl, alkoxy, aryl, and cyano.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device," or sometimes just "electronic device," is intended to mean a device including one or more organic semiconductor layers or materials.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, 81$^{st}$ Edition, 2000).

DETAILED DESCRIPTION

One aspect of the present invention is a composition of Formula I:

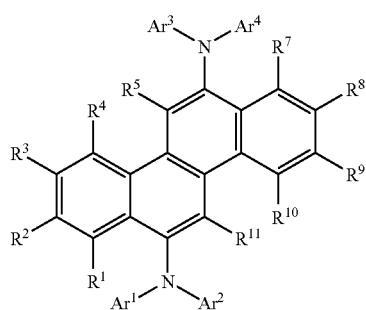

Formula I wherein:

Ar1 and Ar3 are the same or different and are aryl, and at least one of Ar1 and Ar3 has at least one electron-withdrawing substituent;

Ar2 and Ar4 are the same or different and are aryl;

R1, R2, and R4 are the same or different and are selected from the group consisting of H and an electron-withdrawing group;

R3 is an electron-withdrawing group;

R5 and R7 through R11 are the same or different and are selected from the group consisting of H and alkyl.

The compound is capable of deep blue emission.

In some embodiments, the electron-withdrawing group ("EWG") is selected from the group consisting of fluoro, cyano, perfluoroalkyl, perfluoroaryl, nitro, —SO$_2$R, where R is alkyl or perfluoroalkyl, and combinations thereof. In some embodiments, the EWG is fluoro.

In some embodiments, both R1 and R3 are EWGs. In some embodiments, R3, R5, and R7 through R11 are H.

In some embodiments, Ar1 through Ar4 are independently selected from the group consisting of phenyl, biphenyl, naphthyl, and binaphthyl.

In some embodiments, both Ar1 and Ar3 have at least one EWG. In some embodiments, they have two or more EWGs. In some embodiments, both Ar1 and Ar3 are phenyl groups.

In some embodiments, at least one of Ar2 and Ar4 has at least one alkyl substituent. In some embodiments, the alkyl group has 1-8 carbon atoms. In some embodiments, at least one of Ar2 and Ar4 has at least one EWG. In some embodiments, both Ar2 and Ar4 are biphenyl.

In some embodiments, each of Ar1, Ar2, Ar3, and Ar4 has at least one EWG.

In some embodiments, Ar1 and Ar3 are phenyl groups having at least one EWG and Ar2 and Ar4 are biphenyl groups having at least one substituent selected from the group consisting of alkyl and EWG.

In some embodiments, the deep blue chrysene compound is selected from Compound E-1 and Compound E-2:

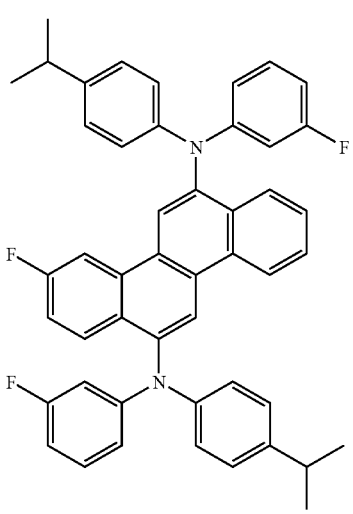

E-1

-continued

E-2

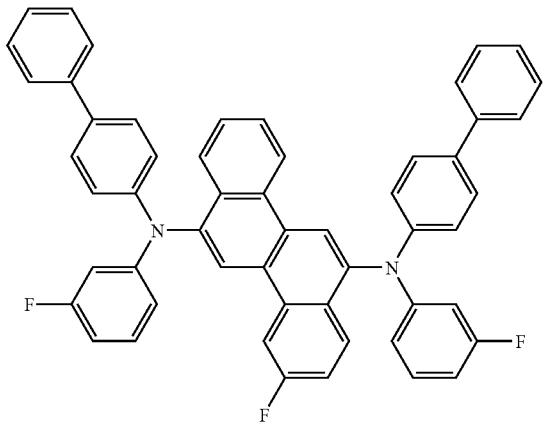

The new chrysenes can be prepared by known coupling and substitution reactions. An exemplary preparation is given in the Examples.

The chrysene compounds described herein can be formed into films using liquid deposition techniques. Thin films of these materials dispersed in a host matrix exhibit good to excellent photoluminescent properties and deep blue emission.

3. Electronic Device

Organic electronic devices that may benefit from having one or more layers comprising the deep blue luminescent materials described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode). These devices generally comprise first and second electrical contact layers with at least one organic active layer between the two contact layers.

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a buffer layer 120. Adjacent to the buffer layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

In one embodiment, the different layers have the following range of thicknesses: anode 110, 500-5000 Å, in one embodiment 1000-2000 Å; buffer layer 120, 50-2000 Å, in one embodiment 200-1000 Å; hole transport layer 130, 50-2000 Å, in one embodiment 200-1000 Å; photoactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the photoactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

a. Photoactive Layer

The chrysene compounds of Formula I are useful as photoactive materials in layer 140. The compounds can be used alone, or in combination with a host material.

In some embodiments, the host is a bis-condensed cyclic aromatic compound.

In some embodiments, the host is an anthracene derivative compound. In some embodiments the compound has the formula:

An-L-An where:
An is an anthracene moiety;
L is a divalent connecting group.

In some embodiments of this formula, L is a single bond, —O—, —S—, —N(R)—, or an aromatic group. In some embodiments, An is a mono- or diphenylanthryl moiety.

In some embodiments, the host has the formula:

A-An-A where:
An is an anthracene moiety;
A is the same or different at each occurrence and is an aromatic group.

In some embodiments, the A groups are attached at the 9- and 10-positions of the anthracene moiety. In some embodiments, A is selected from the group consisting naphthyl, naphthylphenylene, and naphthylnaphthylene. In some embodiments the compound is symmetrical and in some embodiments the compound is non-symmetrical.

In some embodiments, the host has the formula:

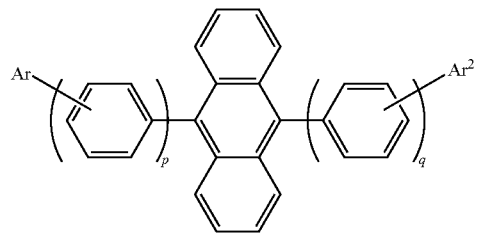

where:
$A^1$ and $A^2$ are the same or different at each occurrence and are selected from the group consisting of H, an aromatic group, and an alkenyl group, or A may represent one or more fused aromatic rings;
p and q are the same or different and are an integer from 1-3. In some embodiments, the anthracene derivative is non-symmetrical. In some embodiments, p=2 and q=1. In some embodiments, at least one of $A^1$ and $A^2$ is a naphthyl group.

In some embodiments, the host is selected from the group consisting of

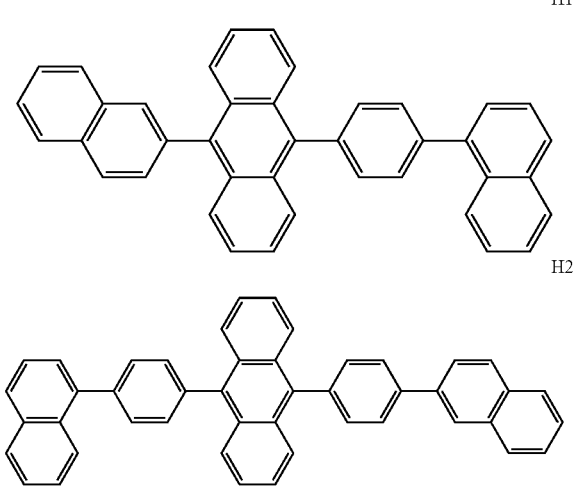

H1

H2 and combinations thereof.

The chrysene compounds of Formula I, in addition to being useful as emissive dopants in the photoactive layer, can also act as charge carrying hosts for other emissive dopants in the photoactive layer 140.

b. Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

The buffer layer 120 comprises buffer material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules. They may be vapour deposited or deposited from liquids which may be in the form of solutions, dispersions, suspensions, emulsions, colloidal mixtures, or other compositions.

The buffer layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The buffer layer can comprise charge transfer compounds, and the like, such as copper phthalocyanine and the tetrathiafulvalene-tetracyanoquinodimethane system (TTF-TCNQ).

In some embodiments, the buffer layer comprises at least one electrically conductive polymer and at least one fluorinated acid polymer. Such materials have been described in, for example, published U.S. patent applications 2004-0102577, 2004-0127637, and 2005/205860

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

Examples of additional electron transport materials which can be used in layer 150 include metal chelated oxinoid compounds, such as tris(8-hydroxyquinolato)aluminum (Alq$_3$); bis(2-methyl-8-quinolinolato)(para-phenyl-phenolato)aluminum(III) (BAlQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. Layer 150 can function both to facilitate electron transport, and also serve as a buffer layer or confinement layer to prevent quenching of the exciton at layer interfaces. Preferably, this layer promotes electron mobility and reduces exciton quenching.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and Li$_2$O can also be deposited between the organic layer and the cathode layer to lower the operating voltage.

It is known to have other layers in organic electronic devices. For example, there can be a layer (not shown) between the anode 110 and buffer layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like. The location of the electron-hole recombination zone in the device, and thus the emission spectrum of the device, can be affected by the relative thickness of each layer. Thus the thickness of the electron-transport layer is desirably chosen so that the electron-hole recombination zone is in the light-emitting layer. The desired ratio of layer thicknesses will depend on the exact nature of the materials used.

The present invention also relates to an electronic device comprising at least one active layer positioned between two electrical contact layers, wherein the at least one active layer of the device includes the chrysene compound of Formula I. Devices frequently have additional hole transport and electron transport layers.

It is understood that the efficiency of devices made with the chrysene compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The chrysene compounds of the invention often are fluorescent and photoluminescent and can be useful in applications other than OLEDs, such as oxygen sensitive indicators and as fluorescent indicators in bioassays.

EXAMPLES

The following examples illustrate certain features and advantages of the present invention. They are intended to be illustrative of the invention, but not limiting. All percentages are by weight, unless otherwise indicated.

Example 1

This example illustrates the preparation of Compound E-1, 3-fluoro-$N^6,N^{12}$-bis(3-fluorophenyl)-$N^6,N^{12}$-bis(4-iso-propylphenyl)chrysene-6,12-diamine.

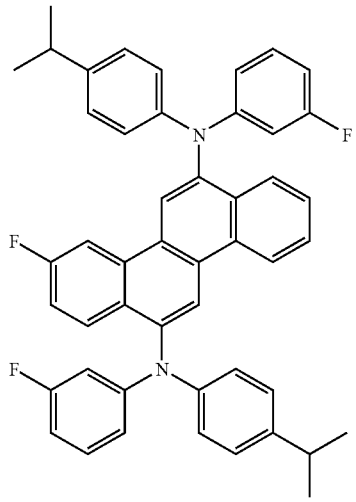

a. Preparation of 1-(4-fluorostyryl)naphthalene

An oven-dried 500 ml three-neck flask was purged with nitrogen and charged with (naphthalen-1-ylmethyl)triphenylphosphonium (11.67 g, 26.6 mmol) and dry THF (200 ml). Sodium hydride (1.06 g, 26.6 mmol) was added and reaction mixture was left to stir overnight at room temperature. Solution was orange in the morning. A solution of 4-fluorobenzaldehyde (3.0 g, 24.2 mmol) in dry THF (30 ml) was added next day (16 h later) over the period of 45 minutes, bleaching the orange-red color. Reaction mixture was stirred at room temperature for 24 hours. THF was removed under reduced pressure. Crude product was purified by column chromoatography on silica gel with 5% $CHCl_3$ in hexanes. The desired product is a mixture of cis- and trans-isomers. Yield 5.7 g (95%) of a viscous oil. The structure was confirmed by $^1H$ NMR spectroscopy.

b. Preparation of 3-fluorochrysene

A mixture of isomeric 4-(2-(naphthalen-1-yl)vinyl)benzonitriles (4 g, 16.1 mmol) was dissolved in 40 ml of dry toluene and transferred into a 1 L photochemical vessel, equipped with a nitrogen inlet and a stirbar. Next, dry toluene (1 L) was added by cannula, followed by iodine (4.17 g, 16.4 mmol) and propylene oxide (100 ml). Two condensers were attached on top of the photochemical vessel. The halogen lamp (Hanovia, 450 W) was turned on. Reaction was stopped by turning off the lamp when no more iodine was left in the reaction mixture, as evidenced by the disappearance of its color. Toluene and excess propylene oxide were removed under reduced pressure to give a yellow solid. The solid was washed with hexane, affording white needles (2.79 g, 70%). The structure of this material was confirmed by $^1H$ NMR spectroscopy.

c. Preparation of 3-fluoro-6,12-dibromochrysene

3-Fluorochrysene (1 g, 3.94 mmol) was placed into a 100 ml round-bottom flask and suspended in 30 ml of $(MeO)_3PO$. Bromine (1.59 g, 10 mmol) was added next. Condenser was attached to the flask, which was brought to 110° C. and stirred for 1 hour. Reaction mixture was then cooled to room temperature and poured into 250 ml of water. The resulting precipitate was filtered again and washed with 100 ml of diethyl ether, giving 4.16 g (91%) of the desired product. The identity of the product was confirmed by $^1H$ NMR spectroscopy.

d. Preparation of E1

In a drybox, 6,12-dibromo-3-fluorochrysene (1.0 g, 2.47 mmol) and 3-fluoro-N-(4-iso-propylphenyl)aniline (1.19 g, 5.2 mmol) were combined in a thick-walled glass tube and dissolved in 10 ml of toluene. Tris(tert-butyl)phosphine (0.09 g, 0.045 mmol) and tris(dibenzylideneacetone)dipalladium (0) (0.02 g, 0.022 mmol) pre-mixed in 10 ml of dry toluene were added next, followed by sodium tert-butoxide (0.476 g, 4.94 mmol) and 10 ml of dry toluene. Glass tube was sealed, brought out of the box and placed into a 80° C. oil bath for 24 hours. Reaction mixture was cooled to room temperature and filtered through a plug of celite and silica. The plug was washed with additional 500 ml of chloroform and 200 ml of dichloromethane. Filtrates were combined and volatiles were removed under reduced pressure to give crude product. Further purification was done by boiling the crude product in 100 ml of hexane and filtering. The resulting white powder (1.25 g or 73.%) was 97.3% pure by LC. The structure was confirmed by $^1$H and $^{19}$F NMR spectroscopy. $^1$H NMR ($CD_2Cl_2$): δ 1.15 (d, 12H, J=6.9 Hz), 2.79 (sept, 2H, J=6.9 Hz), 6.51 (ddt, 2H, J=1 Hz, J=2.6 Hz, J=8.3 Hz), 6.61 (dq, 2H, J=2.2 Hz, J=11.7 Hz), 6.68 (ddd, 2H, J=1 Hz, J=2.2 Hz, J=8.3 Hz), 7.0-7.12 (m), 7.16-7.23 (m, 1H), 7.46 (dd, 1H, J=1 Hz, J=7.7 Hz), 7.55 (dd, 1H, J=1.3 Hz, J=6.8 Hz), 8.0-8.06 (m, 2H), 8.12 (dd, 1H, J=2.4 Hz, J=11.3 Hz), 8.35 (s, 1H), 8.46 (s, 1H), 8.51 (s, 1H, J=8.6 Hz). $^{19}$F NMR ($CD_2Cl_2$): δ −113.72 (m), −113.65 (m), −113.57 (m). PL (toluene, 15 μM): 454 nm. CIE coordinates: x=0.139, y=0.09 (according to the C.I.E. chromaticity scale (Commision Internationale de L'Eclairage, 1931).

Example 2

This example illustrates the preparation of Compound E-2, 3-Fluoro-6,12-N,N'-(4-biphenyl)-6,12-N,N'-(3-fluorophenyl)chrysenediamine.

In a drybox, 6,12-dibromo-3-fluorochrysene (0.7 g, 1.73 mmol) and 3-fluoro-N-(4-biphenylphenyl)aniline (0.96 g, 3. mmol) were combined in a thick-walled glass tube and dissolved in 10 ml of toluene. Tris(tert-butyl)phosphine (0.0065 g, 0.032 mmol) and tris(dibenzylideneacetone)dipalladium (0) (0.015 g, 0.016 mmol), pre-mixed in 10 ml of dry toluene for ten minutes, were added next, followed by sodium tert-butoxide (0.33 g, 3.46 mmol) and 10 ml of dry toluene. Glass tube was sealed, brought out of the box and placed into an 80° C. oil bath for 24 hours. Reaction mixture was cooled to room temperature and filtered through a plug of celite and silica. The plug was washed with additional 500 ml of dichloromethane. Filtrates were combined and volatiles were removed under reduced pressure to give crude product. Further purification was done by boiling the crude product in methanol and filtering. The resulting white powder (1.1 g or 84.6%) was 99% pure by LC. The structure was confirmed by $^1$H NMR spectroscopy. $^1$H NMR (DMF-$d_7$): δ 6.96-7.04 (m, 2H), 7.1 (app tt, 2H, J=1.3, 12.1 Hz), 7.16 (app dt, 2H, J=2.3, 10.3 Hz), 7.50-7.60 (m, 8H), 7.65 (app td, 4H, J=2.1, 7.8 Hz), 7.76 (app td, $^1$H, J=2.5, 8.7 Hz), 7.86-7.98 (m, 10H), 8.41 (dd, 1H, J=1.0, 8.2 Hz), 8.46 (dd, $^1$H, J=6.0, 9.2 Hz), 9.09 (dd, $^1$H, J=2.5, 11.6 Hz), 9.2 (d, 1H, 8.2 Hz), 9.22 (s, 1H), 9.30 (s, 1H). PL (toluene, 15 uM): 451 nm. CIE coordinates: x 0.143, y 0.078.

Example 3

This example demonstrates the fabrication and performance of a device having deep blue emission using Compound E-1 from Example 1. The following materials were used:

Indium Tin Oxide (ITO): 50 nm buffer layer=Buffer 1 (15 nm), which is an aqueous dispersion of polypyrrole and a polymeric fluorinated sulfonic acid. The material was prepared using a procedure similar to that described in Example 1 of published U.S. patent application no. 2005/0205860.

hole transport layer=polymer P1 (20 nm)

photoactive layer=13:1 host H1:dopant E-1 (48 nm)

electron transport layer=Tetrakis-(8-hydroxyquinoline) zirconium (ZrQ) (20 nm)

cathode=LiF/Al (0.5/100 nm)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of Buffer 1 was spin-coated over the ITO surface and heated to remove solvent. After cooling, the substrates were then spin-coated with a solution of a hole transport material, and then heated to remove solvent. After cooling the substrates were spin-coated with the emissive layer solution, and heated to remove solvent. The substrates were masked and placed in a vacuum chamber. A ZrQ layer was deposited by thermal evaporation, followed by a layer of LiF. Masks were then changed in vacuo and a layer of Al was deposited by thermal evaporation. The chamber was vented, and the devices were encapsulated using a glass lid, dessicant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The results are given in Table 1.

Example 4

A device was made and tested according to the procedure of Example 3, using E-2 as the dopant and H1 as the host. The results are given in Table 1.

Example 5

A device was made and tested according to the procedure of Example 3, using E-2 as the dopant and H2 as the host. The results are given in Table 1.

TABLE 1

| Example | CE [cd/A] | Voltage (V) | EL peak [nm] | CIE [x] | CIE [y] | Lum. ½ Life [h] |
|---|---|---|---|---|---|---|
| 3 | 1.3 | 4.3 | 454 | 0.15 | 0.10 | 550 |
| 4 | 1.6 | 6.9 | 454 | 0.14 | 0.11 | 1100 |
| 5 | 1.8 | 6.3 | 454 | 0.14 | 0.11 | 1650 |

*All data @ 2000 nits, CE = current efficiency, LT projected for 1000 nit operation.
P1

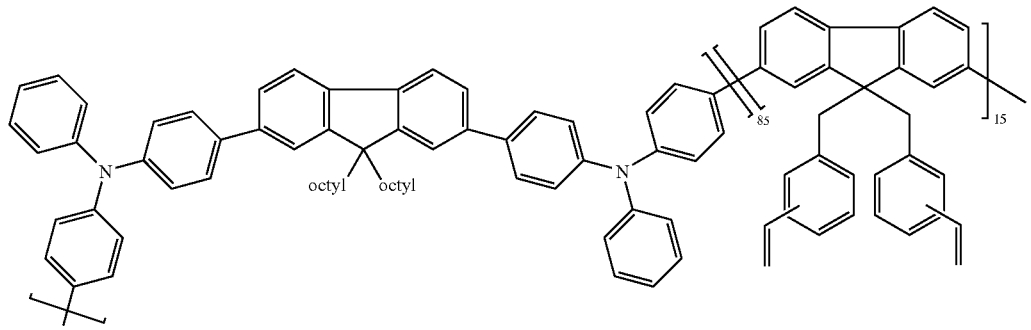

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The use of numerical values in the various ranges specified herein is stated as approximations as though the minimum and maximum values within the stated ranges were both being preceded by the word "about." In this manner slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A compound having Formula I:

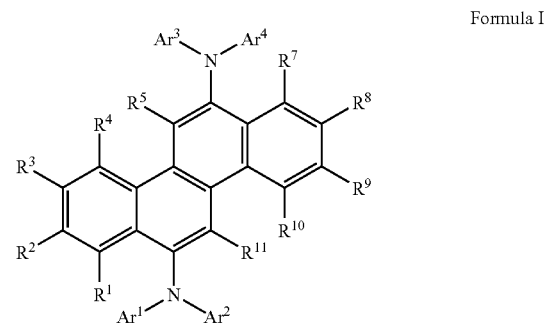

Formula I wherein:
Ar$^1$ and Ar$^3$ are the same or different and are aryl, and at least one of Ar$^1$ and Ar$^3$ has at least one electron-withdrawing substituent;
Ar$^2$ and Ar$^4$ are the same or different and are aryl;
R$^1$ and R$^3$ are electron-withdrawing groups, excluding cyano;
R$^2$, R$^5$ and R$^7$ through R$^{11}$ are H and;
R$^4$ is selected from the group consisting of H and an electron-withdrawing group;
wherein said compound is capable of emitting deep blue light.

2. The compound of claim 1, wherein the electron-withdrawing group is selected from group consisting of fluoro, cyano, perfluoroalkyl, nitro, perfluoroaryl, —SO$_2$R, and combinations thereof, where R is alkyl or perfluoroalkyl.

3. The compound of claim 1, wherein both Ar$^1$ and Ar$^3$ have at least one electron-withdrawing substituent.

4. The compound of claim 3, wherein both Ar$^1$ and Ar$^3$ have two or more electron-withdrawing substituents.

5. The compound of claim 1, wherein Ar$^1$ and Ar$^3$ are phenyl.

6. The compound of claim 1, wherein Ar$^2$ and Ar$^4$ are selected from the group consisting of phenyl, biphenyl, naphthyl, and binaphthyl.

7. The compound of claim 6, wherein Ar$^2$ and Ar$^4$ are biphenyl.

8. The compound of claim 6, wherein at least one of $Ar^2$ and $Ar^4$ has at least one alkyl substituent.

9. The compound of claim 3, wherein $Ar^2$ and $Ar^4$ each have at least one electron-withdrawing substituent.

10. The compound of claim 1, in which at least one of $R^1$ and $R^3$ is halogen.

11. The compound of claim 10, in which $R^3$ is fluorine.

12. The compound of claim 11, in which the compound is E1 or E2:

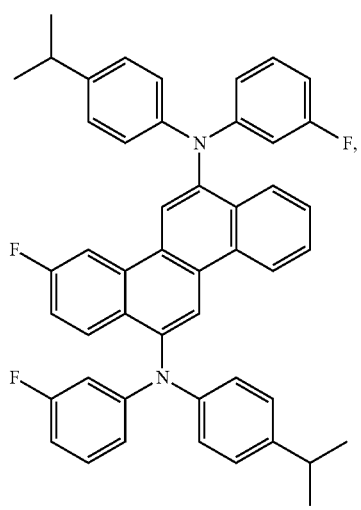

E1

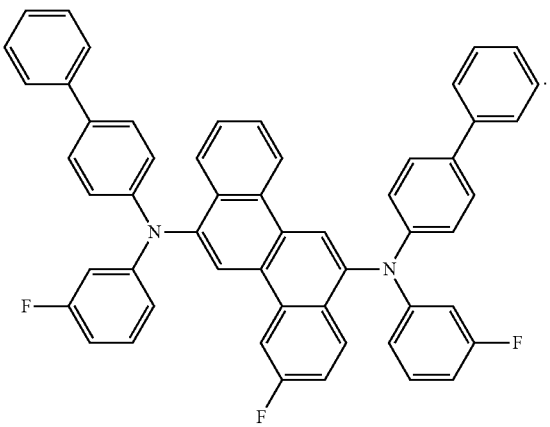

E-2

* * * * *